(12) United States Patent
Hirsch et al.

(10) Patent No.: US 7,269,991 B2
(45) Date of Patent: Sep. 18, 2007

(54) PERMEATION CALIBRATOR

(75) Inventors: Jeffrey A. Hirsch, Bacliff, TX (US); Wallace A. Bruce, Houston, TX (US); Billy G. Gilbert, Deer Park, TX (US)

(73) Assignee: Air Liquide America L.P., Houston, TX (US)

( * ) Notice: Subject to any disclaimer, the term of this patent is extended or adjusted under 35 U.S.C. 154(b) by 119 days.

(21) Appl. No.: 10/780,825

(22) Filed: Feb. 17, 2004

(65) Prior Publication Data
US 2004/0216508 A1 Nov. 4, 2004

Related U.S. Application Data

(60) Provisional application No. 60/447,819, filed on Feb. 14, 2003.

(51) Int. Cl.
G01N 33/00 (2006.01)
G01N 25/00 (2006.01)

(52) U.S. Cl. ...................... 73/1.02; 73/23.25

(58) Field of Classification Search .......... 73/1.02, 73/1.03, 1.04, 1.06, 1.07, 23.21, 23.22, 23.23, 73/23.24, 23.25, 23.26, 854.81
See application file for complete search history.

(56) References Cited

U.S. PATENT DOCUMENTS 3,924,442 A * 12/1975 Kerho et al. ............... 73/23.21
3,976,450 A * 8/1976 Marcote et al. ............... 96/12
4,399,942 A    8/1983 Chand
4,958,529 A * 9/1990 Vestal ....................... 73/864.81
4,977,776 A * 12/1990 Shindo et al. ............... 73/1.03
5,239,856 A * 8/1993 Mettes et al. ............... 73/1.05
5,457,983 A * 10/1995 Sauvageau et al. .......... 73/1.03
5,665,314 A * 9/1997 Berger et al. ............... 422/89

OTHER PUBLICATIONS

Entech Instruments, Inc. online data (http://www.entechinst.com/about.php).*

* cited by examiner

Primary Examiner—Hezron Williams
Assistant Examiner—John Fitzgerald
(74) Attorney, Agent, or Firm—Christopher J. Cronin

(57) ABSTRACT

An apparatus, method, and system for ensuring a more accurate and precise calibration of gas or liquid analyzers using gas emitting permeation tubes for the production of calibration samples. The permeation devices are placed in a temperature-controlled housing to ensure that calibration samples are produced at the optimal temperature for such devices. The housing temperature may be controlled by a semi-conductor heating and cooling device. The apparatus also controls the flow rate of the medium that is mixed with the impurities released from the permeation devices, yielding a more accurate, precise, and reliable calibration. The sample can be conveyed to the calibration device/instrument by hooking the apparatus directly to the calibration device. The invention also contemplates a novel method of calibrating apparatuses using a device kept at the optimal temperature, using a constant flow rate that minimizes variations in the calibrations.

8 Claims, 4 Drawing Sheets

PERMEATION CALIBRATOR

RELATED APPLICATIONS

This application claims priority from U.S. Provisional Application No. 60/447,819, filed 14 Feb. 2003.

BACKGROUND

This invention relates generally to an apparatus and system for producing a more accurate calibration gas that is used to calibrate analytical instruments. A method of producing such calibration gas is also contemplated. This invention enables enhanced quality control and product end quality. The apparatus and system are particularly well suited for devices that emit gas(s) at a constant rate, and particularly, to commercially available gas emitting devices that are used to produce calibration gases for various types of gas or liquid analyzers. The gases are typically emitted from such a device through a permeable material, and mixed with a moving fluid medium, such as gas to form a calibration standard for use in an analyzer or other instrument.

As such, control of the temperature environment where such devices are used is extremely important to get a more reliable and steady diffusion of such standards, and further as such standards are relatively expensive, the reliable life of the standards can be prolonged by keeping the standards in a temperature controlled environment.

In prior art practices, it was not uncommon to leave the permeation devices in ambient air temperatures when the devices were not being used. Further, it was not uncommon to use tubing that connected a gas source to the permeation device and then to the instrument, mid-air and subjected to varying ambient air temperatures. Further, if an air conditioner or heater turned on, or the ambient room temperature was otherwise changed, the permeation device would be subjected to varying temperatures. The temperature would often be measured at the point of the tube hanging in mid-air, which would not be entirely accurate because sudden temperature changes could change the characteristics of the permeation device. Further, gas flow might be estimated, or a flow meter might be used.

Also, the permeation devices might have been subjected to different temperatures overnight (cooler or hotter temperatures, e.g., due to seasonal temperatures), even though climate control systems may have warmed or cooled the environment a few hours or less before use. Thus, the permeation device might take hours, or even half a day to actually reach equilibrium and a steady diffusion rate. Thus, by keeping the permeation device at a constant, controlled temperature, the devices are not subjected to temperature extremes that can cause miscalibrations.

Importantly, another critical parameter for proper operation of the permeation standard is the flow rate. Applicants' apparatus, method, and system include a means for controlling the flow rate of the fluid medium as well as the temperature of the permeation device and the gas that mix with the impurity source.

Preferably, a semi-conductor cooling and heating device is used in conjunction with Applicants' invention. The semi-conductor device is small, efficient, and economical to use.

While certain prior art apparatus exist, they are limited in their function. For example, the prior art apparatus and methods only include heating means, while Applicants' invention also focuses upon cooler temperatures ranges. This is especially advantageous for certain types of permeation devices and in situations where the ambient temperature exceeds the optimal temperature range for operation of the permeation devices.

Furthermore, because the apparatus and system is preferably kept in an operative standby mode when calibration is not needed, the apparatus can be easily and quickly shifted to a calibration mode by changing the source of gas that flows through the apparatus and system.

DETAILED DESCRIPTION

Figure 1:
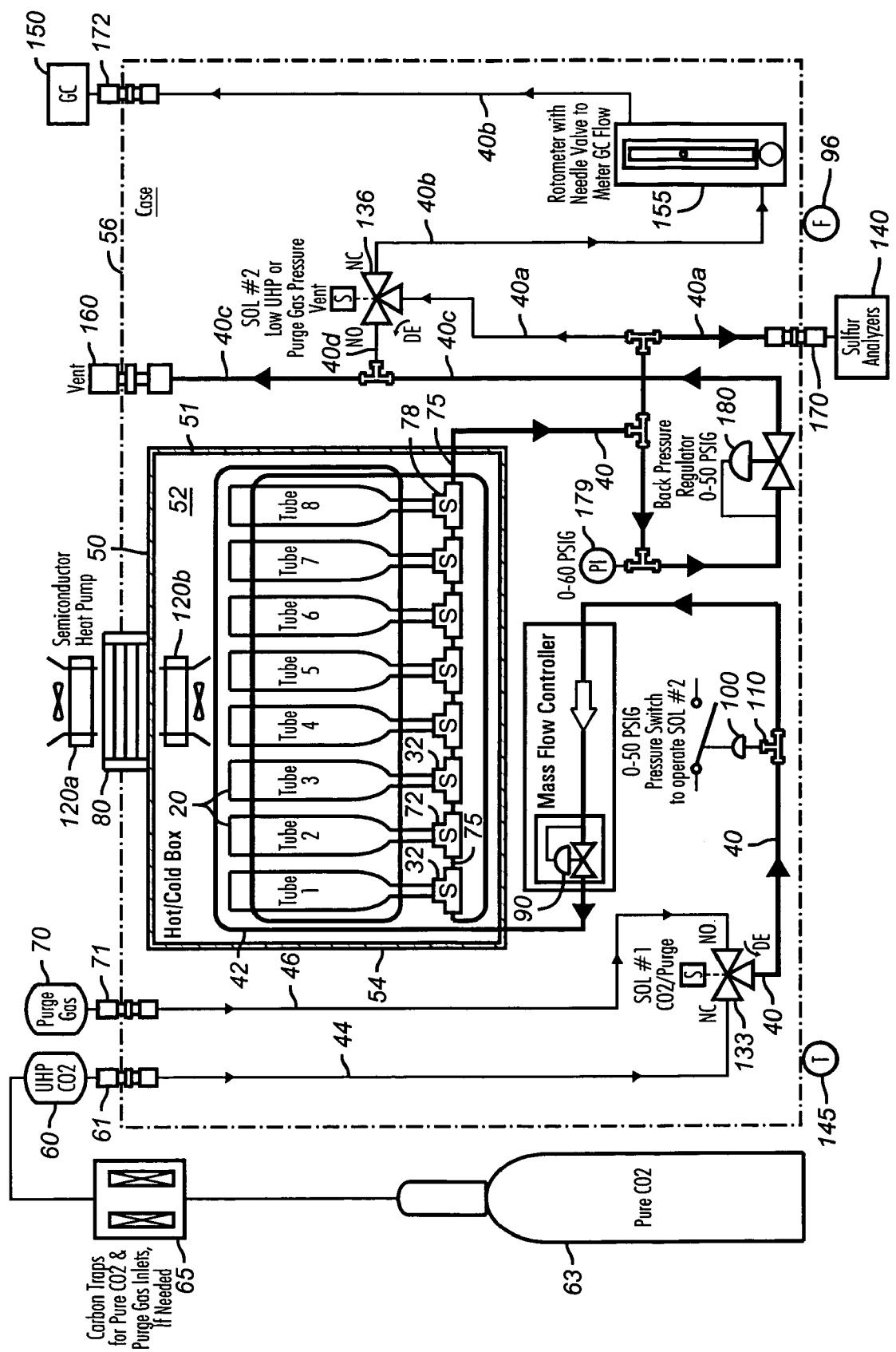
FIG. 1 shows an embodiment of an apparatus of the invention.

For purposes of the description of this invention, the terms "upper," "front," "back," "downstream," "end," and other related terms shall be defined as to relation of embodiments of the present invention as it is shown and illustrated in the accompanying figures. However, it is to be understood that the invention may assume various alternative structures and processes and still be within the scope and meaning of this disclosure. Further, it is to be understood that any specific dimensions and/or physical characteristics related to the embodiments disclosed herein are capable of modification and alteration while still remaining within the scope of the present invention and are, therefore, not intended to be limiting.

Certain commercially available permeation devices operate especially well at room temperature, but controlling room temperature or other environment temperatures are difficult because of temperature changes due to fluxuations caused, for example, by heating and cooling systems turning on and off, and seasonal changes. To solve this problem, Applicants came up with a method of generating an elevated false temperature and then using a semi-conductor cooling device to lower the temperature to a range between about 60° F. and about 80° F. to and even more preferably to a range of about 75° F. to about 77° F. Because the semi-conductor device can also be used to produce heat, the apparatus can also be used to maintain high temperatures, if desired.

This invention relates generally to an apparatus and system that more accurately produces a calibration gas for calibrating analytical instruments, and a related method. The apparatus and system are particularly well suited for permeation devices/standards that emit gas(s) at a constant rate, and particularly, to such commercially available emitting devices used in the production of calibration gases or liquids. The gases are emitted from such a device through a permeable material, and mixed with a moving fluid medium, such as gas for use in an analyzer or other instrument.

Because Applicants' invention is capable of heating, cooling, and maintaining the temperature of the environment where the permeation devices are housed, more accurate calibrations and analyses can be accomplished. Further, due to controlled temperature and flow conditions, the permeation devices may have a longer life. Further, permeation devices of various designs, types of standards, and concentrations requiring of varying temperature ranges can be used reliably.

The apparatus is also designed for a combination of duties for different analyzers. For example the apparatus can be used to accurately calibrate a gas chromatograph and sulfur analyzer for carbon dioxide, which is especially critical for low concentrations like parts per billion.

One such device disclosed that is capable of emitting a gas at a constant rate into a moving fluid medium to produce an accurately known concentration of the gas in such medium is U.S. Pat. No. 4,399,942 by Chand. The device includes a sealed vessel, in which a substance to be emitted is stored under pressure, and a quantity of permeable material through which the stored substance permeates at a predetermined rate. The gas is held in a cylinder that has two chambers. One of the chambers holds the substance in liquefied form and the other chamber holds the substance in gaseous form. The gas and liquid substance permeates through a permeable material between the two chambers and then through another quantity of permeable material that is positioned at an exit from the second chamber. That device dispenses a gaseous substance at a constant rate, the gas thereafter being mixed with a moving fluid medium to provide a calibration gas containing a known concentration of the gas at a predetermined flow rate and at a certain temperature range. The temperature range is specified by the manufacturer of the sources/permeation devices. The sample is then typically used to calibrate an analyzer of gases or liquids.

FIG. 1 shows an embodiment of an apparatus of the invention. The apparatus comprises at least one source 20 such as a permeation device/standard that generates at least one chosen impurity in a known range of nanograms per minute within given temperature ranges and at a known or predetermined flow rate. Because the diffusion rate of such devices is temperature and flow dependant, they should be used at the temperatures and flows recommended by the manufacturer. For expediency in preparing a calibration gas, they should also be maintained at the suggested the temperatures and flows rate when calibration is not needed and the apparatus is in standby mode.

As in FIG. 1, a main conduit 40 runs through the apparatus and that provides a source of fluid media to mix with the impurity source, such as a supply of pure gas 50. The main conduit may be a variety of sizes, such as between ⅛" and ½" or other diameters that are known or used by one skilled in the art for producing calibration gases or liquids for analyzers. However, ¼" tubing has been found to be preferable. Further, there is a communication 32 between the impurity source 20 and at least a portion of the main conduit. Gas flows through the main conduit and passes by the communication, wherein the impurity from the source diffuses into the gas that flows past the communication. If pure gas is used in the apparatus, a calibration gas 78 can be produced. Further, the apparatus has a housing 50 having an interior 52, wherein the impurity source and at least a portion of the main conduit is located within the interior of the housing. The impurity source mixes 72 with the gas in the conduit that passes by the communication.

The apparatus of may further comprise a first gas conduit 44 and a second gas conduit 46, with and a valve, e.g. 133, connecting the first and second conduits to the main conduit. See FIG. 1. Further, connector 61 may be used to connect the source of pure gas 60 to the first conduit 44, and connector 71 may be used to connect the supply of purge gas 70 to the second conduit 46. The connectors may be quick connectors, fittings, couplings, or any other such devices known or used by one skilled in the art for such purposes. In this embodiment, pure gas 60, such as carbon dioxide, is introduced into the first conduit 44 when calibration is desired and purge gas 70 can be introduced into the second conduit 46 when calibration gas is not needed. The valve 133 or other control means that is known or used by one skilled in the art determines which gas will flow into the main conduit.

The temperature within the housing interior 52 is maintained between about 60° F. and about 100° F. during standby or when calibration is desired, by cooling or heating the interior as needed. Further, the temperature within the housing interior can be maintained between about 75° F. and about 77° F. during standby or when calibration is desired.

The apparatus may have a temperature indicator 145 that can also be changed to set the desired temperature.

Other tubing sizes may be used within the apparatus. For example, if there is a first conduit and a second conduit leading to the main conduit, which in an embodiment is ¼" tubing, the tubing of the first and second conduits are preferably ⅛". Also, tubing that leads to the sulfur analyzer 140 is preferably ¼", with the tubing leading to the gas chromatograph 150 being ⅛". Of course, tubings of other diameters that are known or used by one skilled in the art for producing calibration gases or liquids for analyzers can also be used.

Figure 2:
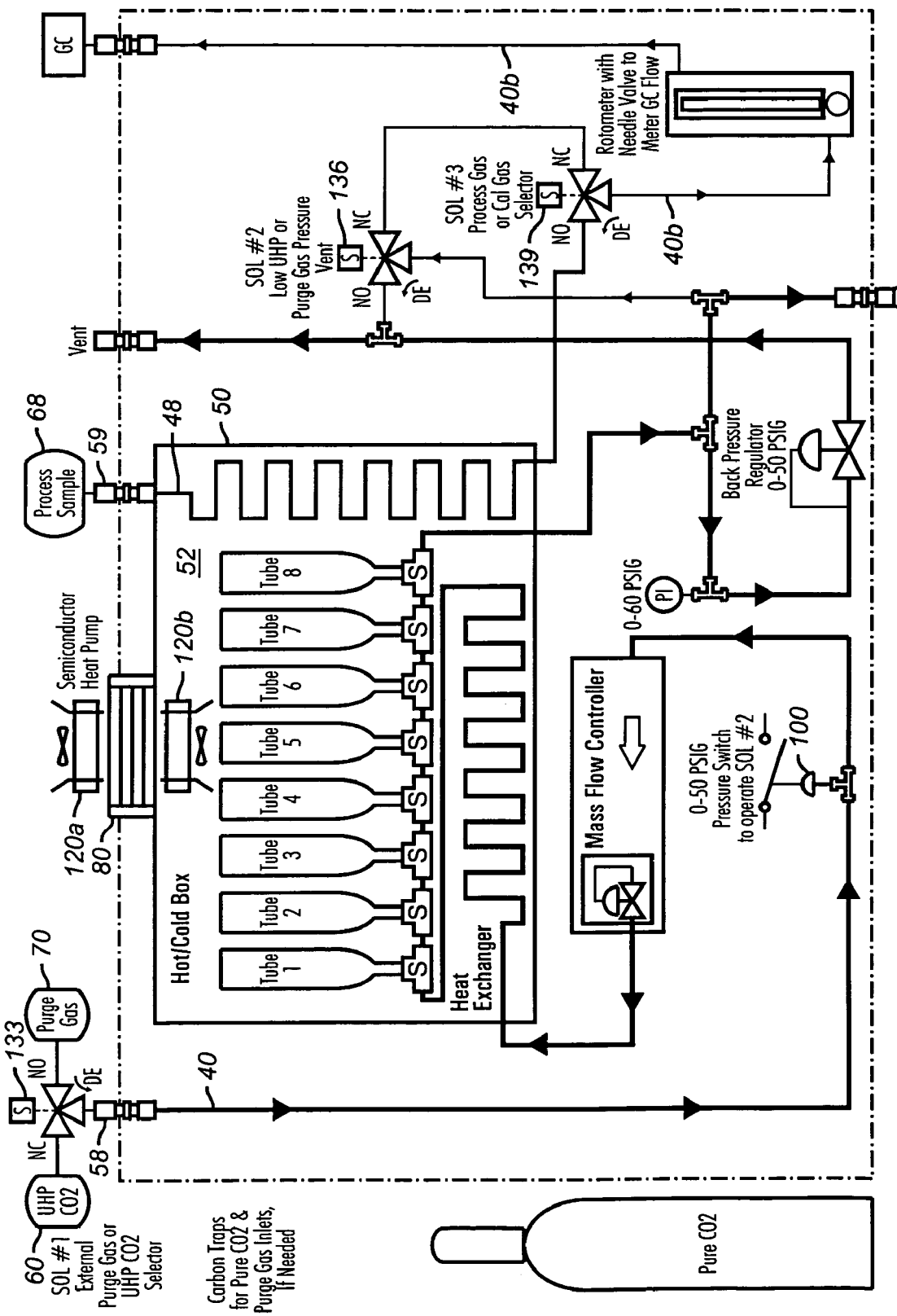
FIG. 2 shows an alternative embodiment of an apparatus of the invention.

A variety of tubes or devices that produce a known and reliable standard for a variety of impurities may be used. Also in the apparatus, the impurity source may be placed in a header 78 or manifold that is located within the housing and that communicates with the conduit. See FIGS. 1-2. The apparatus may hold a plurality of permeation devices that each produces a different impurity.

Further, a plurality of headers may be used, wherein each header holds a different source. While the apparatus my hold any number of permeation devices/impurity sources, limited only by the size of the apparatus and/or the housing, an apparatus with the capability to hold up to 8 or up to 16 different sources has been found to be especially useful.

If a plurality of devices is used, with each device emitting a different impurity, then the calibration gas can be used to calibrate a variety of instruments and/or for a variety of parameters. Because the concentration of the impurities is so small, ranging in nanograms per minute, the use of more than one impurity in the calibration gas does not cause significant error with regards to the concentrations of the other impurities The impurity source may comprise any type of impurity for which testing is desired and varies upon the type of samples to be tested. For example for non-hydrocarbon gases, such as carbon dioxide, a common impurity that is undesired and which is commonly monitored is hydrogen sulfide. As a further example, for natural gas that is used for heating or cooking an undesired component would be benzene or carbon monoxide. Other types of common impurities include, but are not limited to gases consisting essentially of acetaldehyde, dimethylether, carbonyl sulfide, dimethyl sulfide, or a combination thereof. Further, the devices that produce the impurity standard may supply at least one impurity, or a multitude of impurities.

A variety of components can be tested for such as sulfur, benzene, acetaldehyde, dimethylether, and methanol. Typically, there are four common basic components, tested for in gas production plants. The apparatus may hold a single tube, but more advantageously holds a plurality of devices that are in series.

Types of impurity sources that are used in this apparatus, system, and method include, but are not limited to components that are monitored during industrial processes, manufacturing, research and development, gas production, and the like, and any other applications in which gas is tested, and includes but is not limited to: acetaldehyde, acetic acid, acetone, acetonitrile, acrylonitrile, ammonia, arsine, benzene, boron trichloride, boron triflouride, 1,3-butadiene, n-butane, t-butyl mercaptan, sec-butyl mercaptan, butyl mercaptan, carbon dioxide, carbon disulfide, carbon monoxide, carbonyl sulfide, chlorine, chloroform, di-iso propyl methyl phosphonate, di-methyl methyl phosphonate, diethyl sulfide, dimethylether, dimethyl disulfide, dimethyl sulfide, ethanol, ethyl mercaptan, ethylene oxide, formaldehyde (para), freon-11, freon-21, hydrazine, hydrogen chloride, hydrogen fluoride, hydrogen sulfide, iodine, methane, methanol, methyl chloride, methyl mercaptan, methylene chloride, nitric oxide, nitrogen dioxide, nitrogen triflouride, nitrous oxide, oxygen, phosgene, phosphine, propane, propyl mercaptan, propylene oxide, silane, silicon tetrachloride, silicon tetraflouride, styrene, sulfur dioxide, thiophene, toluene, vinyl acetate, vinyl chloride, water, m-xylene, o-xylene, p-xylene. The impurities used for calibration will likely be based upon impurities that are expected to be present in samples, which have an unknown amount of impurities therein. The impurities tested for may consist essentially of any the foregoing elements and compounds or a combination thereof.

One such device is a G-Cal Permeation tube made by Vici-Metronics. The G-Cal tubes are covered by U.S. Pat. No. 4,399,942, entitled Gas Emitting Device by Chand. That patent is incorporated fully by reference herein. Chand discloses a device for emitting a gas at a constant rate into a moving fluid medium to produce an accurately concentration of the gas in the medium that is known. Further, the G-Cal tubes have a reservoir full of liquid, permeation wafers, and a regulated orifice size.

Figure 3:
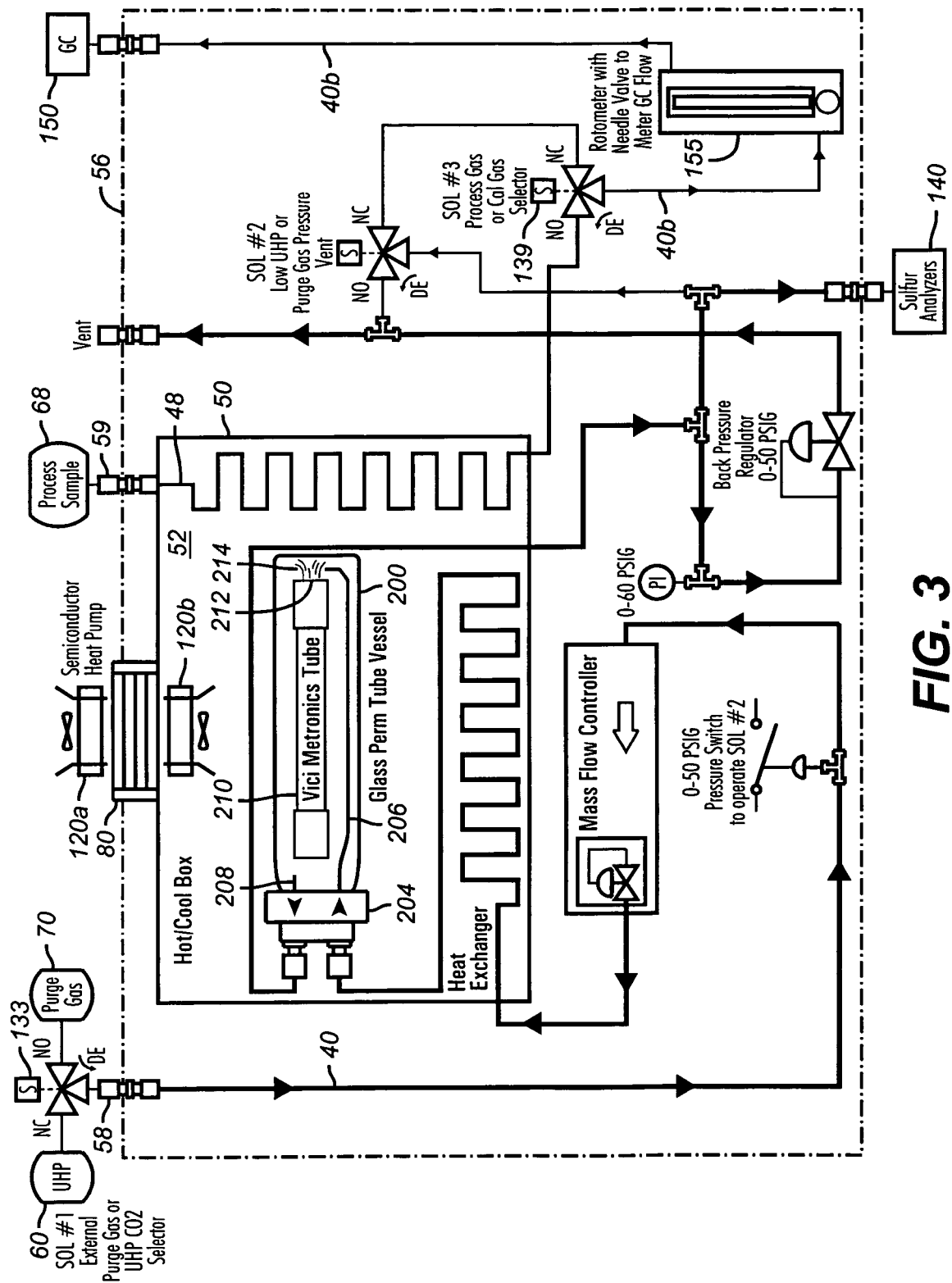
FIG. 3 shows another alternative embodiment of an apparatus of the invention.

Vici-Metronics also makes a Metronics tube, which is a Teflon permeation tube, but it has to be at around 90° F. or higher to generate its chemical output. In an embodiment of the invention one preferred tube is used at about 70-77° F., while another tube is used at about 90° F.-130° F. Further, with the chiller capability, if the temperature is turned down, will not permeate the tube, so it will last a lot longer than this one. The G-Cal tubes/devices will always permeate opposed to the Metronics devices. The Metronics devices can be put into a chill mode and kept cool until the day before they are ready to do calibration. The G-Cal tubes screw into a header, and permeates into the header and the passing gas flow picks it up. See e.g., FIGS. 1-2. For the Metronics tube, the flow goes across it and comes back out, and requires a different arrangement. See FIG. 3. As shown in FIG. 3, the Metronics tube is placed inside a glass vessel 200 with an opening having a stopper. In an embodiment, the stopper screws on. The stopper is equipped with an inlet conduit 206 the length of the glass vessel and a short outlet conduit. 208. The gas flow passes through the long conduit 206 to the end of the glass vessel and then passes over the Metronics tube 210 sweeping the permeated impurity 214 out the vessel outlet 212. Other materials that are known or used by one skilled in the art for such vessels that hold such permeation devices may also be used.

Typically, a certificate is included with each tube or device, identifying the type of impurity, the flow to be used, the temperature to be used, and all the specifications needed for this tube, as well as the date of production and/or date that the tube was put into service. This helps keep track of the age of the tube so that they changed out about once a year. The concentrations of the source can be specified and the permeation rates may for example range from about 10 to about 50 nanograms per minute, even up to 50,000 nanograms (ng) per minute or higher. Of course other rates and ranges that satisfy the particular type of samples being analyzed may vary and can be specified by one skilled in the art. The impurity sources produce a calibration gas that is measurable in ppm, ppb, or even ppt. Other devices that emit standards used for testing may also be used such as those produced by KEN-TEK, Dynacal, Calibrage, and other such devices that are commercially available or known to one skilled in the art.

Other impurity standards that exist that are known to one skilled in the art may also be used. With respect to the sulfur impurity, carbonyl sulfide is used as the sulfur standard because it is safer than hydrogen sulfide and it satisfies the total sulfur analysis needs.

Depending upon the characteristics of the impurity devices, it may be preferable to leave such devices within the housing. Because flow-fluctuations or temperature fluctuations affect the devices, if they are not at a certain temperature and are not diffusing at a steady rate, they will not be ready, to use when calibration is needed and thus they may cause unreliable or erroneous calibrations. Since certain permeation devices such as the G-Cal tubes are always permeating regardless of external flows or temperature, it is important to keep them in an environment with a constant temperature and flow, so that they have a steady permeation rate. Controlled flow is important during standby and especially during calibration. If the flow is increased, gas is taken off the surface of the permeation wafer. In contrast, is the flow is decreased, it takes longer for the permeation wafer to adjust to the lesser flow, and the lesser flow has a siphoning-like effect. Applicant's method of controlling the flow ensures that the devices will be ready when calibration is needed.

In addition, there is a means for selectively raising and/or lowering the temperature of the housing interior between about 60° F. and 130° F. so as to create the optimal temperature in the housing for the calibration source 20. A temperature controller controls the temperature of the means for raising or lowering the temperature of the housing. See e.g. FIG. 4. The temperature controller may have readout, such as a digital readout, and it may be adjusted by knobs or push buttons. Other types of temperature controllers known or used by one skilled in the art may also be used.

In an embodiment of the apparatus, the temperature within the housing interior is maintained between about 75° F. and about 77° F. during standby and/or during calibration. In an embodiment, the temperature within the housing interior is heated and/or cooled between 60° F. and about 130° F. during standby and/or during calibration.

In a preferred embodiment, the means for selectively raising and/or lowering the temperature is comprised of a semi-conductor heating and cooling device 80. This allows one to use two different types of permeation devices, one that works well in the approximately 70° F. to approximately 80° F. ambient room temperature, and another that has to be operated up around 90° F. in one apparatus.

The temperature of the interior 50 of the housing 52 of the apparatus is controlled by a temperature controller. In an embodiment, a semi-conductor heat pump operates to elevate, lower, or maintain the temperature within the housing. The apparatus is also suited for permeation devices that operate in varying temperature ranges. If necessary, heat can be generated to bring the temperature above the normal ambient temperature, then the temperature within the housing is lowered or is cooled down.

Figure 4:
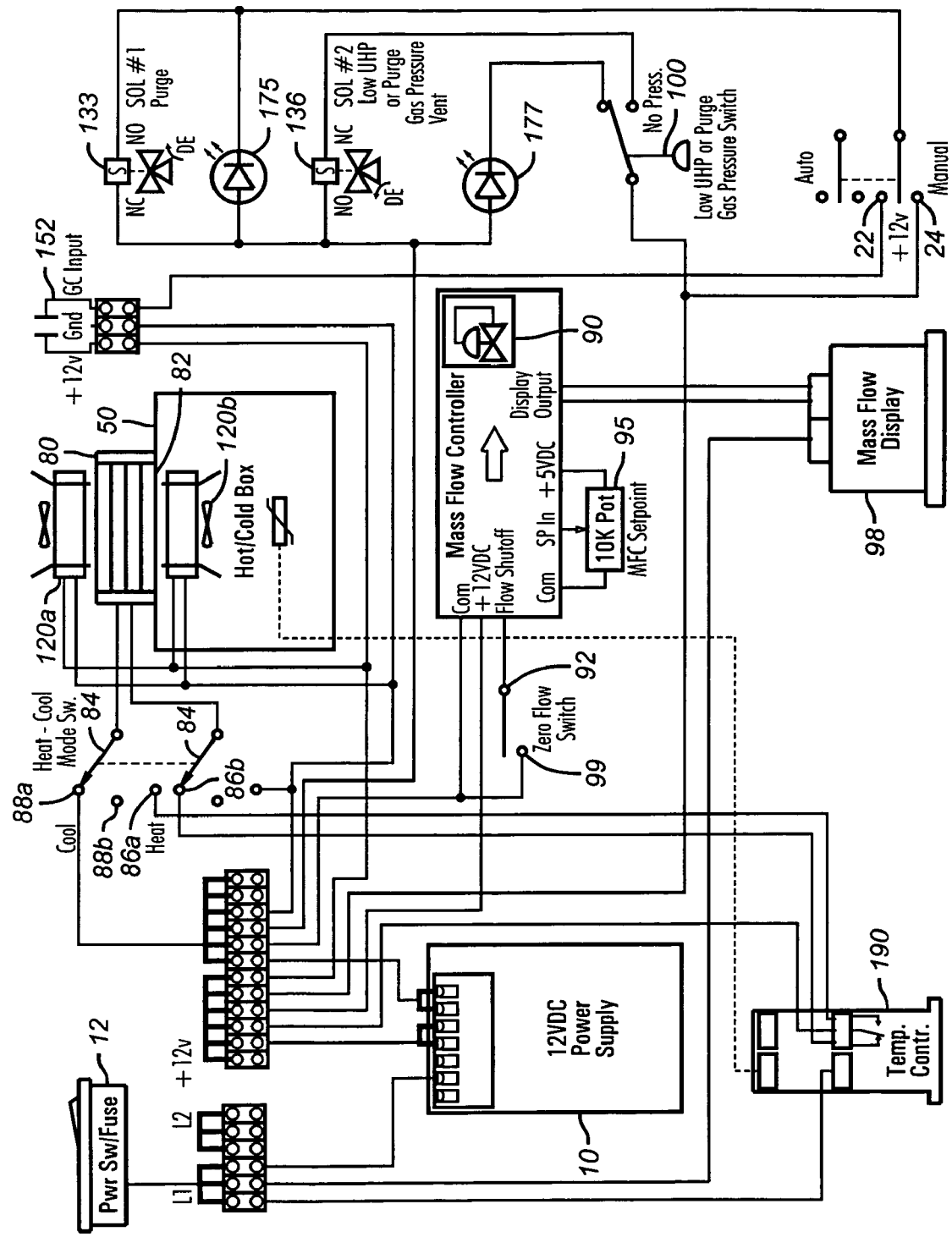
FIG. 4 shows the circuitry of an embodiment of an apparatus of the invention.

The apparatus preferably has a switch that controls the semi-conductor device and determines whether the device produces heat or cooling. The semi-conductor heating and cooling device is considered a heat pump. By merely flipping a switch and reversing the voltage, heat or cooling can be generated. See FIG. 4. The switch for the semi-conductor device is manually controlled and/or automatically controlled. FIG. 4 shows the circuitry of a semi conductor device in the cooling made with point 88a in circuit, and the heating circuit opened at point 86b. In the heating mode, the cooling circuit would be open at point 88b, and the heating circuit closed at 86a. A length of conduit 42, preferably at least about 6 feet to 8 feet is located within the housing in advance of the source so that the gas travelling through the conduit can be equilibrated to the same temperature of the housing and the source in the housing to provide a medium that is about the same temperature or is the same temperature as the housing interior and the source. See FIG. 1.

If more heating or cooling capabilities are desired, the semi-conductor devices can be stacked upon each other. Within the device, there is a ceramic semi-conductor heat pump attached to a metal thermal transfer plate, which withdraws or imparts heat to the housing. By stacking the additional ceramic semi-conductor modules higher or lower temperatures can be obtained Other heating and cooling apparatuses known or used by one skilled in the art can also be used to heat, cool, or maintain the desired temperature in the housing, such as, Vortex chillers, or other refrigerant devices for cooling; silicon heater strips and wire wound heater cartridges for heating.

Further, the apparatus preferably has a flow controller, such as a mass flow controller 90. The flow controller maintains a steady flow of gas in the conduit and communication by the source. In an embodiment, the mass flow controller is a set by point tensiometer, which provides a set point, and controls the flow. Also, a flow meter may be used to display or set the gas flow. In an embodiment this flow meter 96 is on the front of the apparatus. In an embodiment, the normal flow is about 0.5 liters per minute to about 1 liters per minute, with capabilities for zero liters/minute to about 2 liters/minute capabilities. When the gas passes by the communication of a header that holds a source, such as a permeation device and as it passes by each device, it picks up that component. Of course the apparatus can be run without having a source in each header.

In an embodiment of the apparatus, there is a source of purge gas can be run through the main conduit and past the impurity source when the apparatus is on standby. See e.g., FIGS. 1-3. Thus, even when the apparatus is on standby, the permeation device has a constant diffusion rate and the impurity from the source diffuses into the purge gas. Because the permeation from the impurity source is constant, the output of the impurity is the same regardless of the type of gas flowing through the conduit, as long as the flow rate and temperature are the same for the purge and pure gases.

In an embodiment, the source of purge gas is from normal plant or gas production. Additionally, during normal gas production processes, the purge gas will be just as clean and the pure bottled gas.

Of course pure or nearly pure gas could also be used as a purge gas, but since pure gas is expensive, a less expensive source of gas is preferred for a purge gas. The gas that is being produced by gas may also be nearly pure.

In an embodiment, the purge gas may be comprised essentially of carbon dioxide, nitrogen, oxygen, helium, argon, carbon monoxide, hydrogen or a combination thereof. Other gases, which are also suitable for use as a purge gas that are known or used by one skilled in the art, may also be used.

In an alternative embodiment, the purge gas 70 and the pure gas 60 are introduced into the main conduit 40 at different times. See FIG. 2. A valve, such as a solenoid valve 133 is used to connect the gas supplies to the main conduit 40 and to control which gas will flow into the main conduit. The valve is connected to connector 58.

The apparatus is most cost efficient with at least two types of gas coming in. In an embodiment, one gas is ultra high purity (UHP) bottled liquid $CO_2$, which is liquid, and the other is purge gas that is a stream from the plant gas production. The choice of the pure gas may vary depending upon availability. Further, the choice of the pure gas may be based upon the expected type of gases within the samples that will later be analyzed by the instruments. The types of purge gas may come from different sources. Preferably, the purge gas has low levels of impurities. Further, if desired, a carbon trap 65 may be used to filter certain impurities in the purge gas or pure gas prior to entry into the conduits.

Because UHP gas is bottled and is expensive, a purge gas, such as that comes from plant production is used in the apparatus during standby. The purge gas is used to maintain a constant purge across the permeation devices such as the G-Cal tubes. The two gas lines lead to a valve, such as a solenoid valve 130 which switches between the lines and which allows the operator to select either the UHP purge gas or the ultra high purity (UHP) $CO_2$. When it is time to calibrate, the UHP $CO_2$ gas is selected.

Unless flowing pure gas is used to purge the apparatus during standby, when calibration is desired pure gas must be run through the conduit. Further, to fully clear the conduits of purge gas, only a short time interval, typically a few minutes is involved because there is not a great length of tubing. The impurity then mixes with the pure gas in the conduit to provide a calibration gas. Downstream from the impurity source, the calibration gas is conveyed through the conduit to an instrument. If desired, the tubing can be coiled to fit within the housing.

If the temperature and flow parameters are appropriate, the instrument can analyze the calibration gas for purposes of instrument calibration. The instrument can then be calibrated based upon the results of the analysis and the known concentration of the source at a certain temperature range and flow rate.

More than one instrument can be used to analyze the calibration gas and the results of the various instruments may be compared. The comparison may suggest further calibration steps, verification of the sample results, replacement of the sources, or repair of the involved instruments or apparatus. Further, at least one instrument can be calibrated based upon results of the analysis and the known concentration of the source at a certain temperature range.

After the gas exits from the header are, and the housing 50, there are several options for channeling the calibration gas. Also, a backpressure regulator may be connected to the conduit prior to the instrument. In an embodiment, the pressure is kept at approximately 40 psi to maintain the correct pressure to operate the intact total sulfur analyzers that require about 30 psi to about 35 psi of pressure on the inlet. The calibration gas comes out as a combined gas, which then brings them to out to a small header, which has a back pressure regulator on it, which is what is used to actually hold the approximately 40 psi of back pressure, so that there is constant pressure, constant flow and then all of this is controlled, with a temperature controllers, so that constant temperature is maintained. If the pressure of the gas is less than the desired pressure, it will be vented at vent 160 through conduit 40c. See FIG. 1.

For example in an embodiment, there are two options for directing calibration gas. The gas conduit 40a may lead to a sulfur analyzer or to the solenoid valve 136. If the pressure is less than about a 40 psi or another desired set point, valve 136 will de-energize and the gas will flow into conduit 40c to vent 160. The conduit that exits the housing leads to a solenoid valve 136, a three-way solenoid valve with a conduit 40d leading to the normally open side of the valve, and then breaks into at least two branches e.g. 40a, 40b. These branches may lead to analytical instruments. See FIG. 1. Branch 40b can lead to another quick disconnect device 172 that can be used to connect to another type of instrument such as a gas chromatograph 150. The side of the valve leading to branch 40b is normally closed. Of course, other types of connections known or used by one skilled in the art can be used in place of the quick disconnect devices. Under normal operating conditions, as long as the zero psi to 40 psi pressure switch is satisfied, there will be gas flow to, for example, gas chromatographs. Other configurations of the conduits are also possible.

Once the instrument is calibrated, various samples may be analyzed. The samples comprise gases or liquids that contain an unknown amount and/or type of impurity for analysis. The results of the analysis of the calibration gas and/or sample gas is typically displayed by the instrument on a readout such as a LCD display, and may also the results on paper, or such data may be stored in a computer.

In an embodiment, the apparatus has a first 44 and a second gas conduit 46, wherein the first conduit is connected to a source of pure gas 60 and the second conduit is connected to the source of purge gas 70. See FIG. 1. The first and second conduits are then connected to a main conduit 40.

In an alternative embodiment, a supply of pure gas 60 and a supply of purge gas 70 are both connected directly to the main conduit 40. See FIGS. 2-3.

In an embodiment, a pressure switch 100 may be incorporated into the conduit prior to the permeation devices and the gas flow is preferably set to about 50 psi. Once the gas reaches 40 psi or below, then the pressure switch causes the excess flow to exit or pass out of the vent 110. This ensures that same flow rate or steady flow rate is maintained across the permeation devices. This pressure switch also ensures that insufficient pressure, leading to improper flow across the permeation devices is vented and does not cause faulty analyzer calibration. Further, it is desirable to maintain the constant flow across the tubes even though it is not necessary to use the full one-liter calibration gas in the analyzers; thus, the unused excess calibration gas is vented through the backpressure regulator 180.

The apparatus of this invention may also be used in conjunction with an instrument to be calibrated, wherein the conduit provides a circuit for the calibration gas, and wherein the calibration gas is fed to an instrument that analyzes the gas, e.g. 140, 150. See FIG. 1.

Also, a chart having the known concentration of the impurity in ppm or ppb at certain temperature ranges and the flow rates from the source may be used in conjunction with the results of the calibration to calibrate the instrument(s). The chart has a range of values of such impurity. The variables include temperatures and flows, the type of permeation tube, and rate of permeation such as nanograms per minute, which equate to ppm, ppb, or ppt. The chart may also include other data such as the serial number and manufacturer. A sheet may be made for each permeation tube, and the ultimate concentration of the standard in ppb or even ppt can be readily known at certain temperatures and flow rates.

The apparatus of this invention may further comprise means to connect to the apparatus to an instrument that analyzes the calibration gas. The means that connects the apparatus of this invention to the instrument may comprise a variety of means such as a conduit that leads to a device such as a quick connector that directly connects to the analytical instrument, or another type of connector that accepts tubing that joins the instrument to the apparatus. Of course the conduit that exits the housing may lead directly to an instrument. The conduit may also exit the apparatus or lead to another conduit that exits the apparatus.

Further, the apparatus may have means to vent gas 160, such as a vent, pressure valve, or from the housing to the main conduit if the pressure of the calibration gas drops below about 40 psi. Further, the apparatus may be programmed or controlled to also vent the gas if it rises above about 100 psi, but that is not typically a problem as there is a pressure regulator on the pure gas to control the gas pressure. If the pressure drops below about 40 psi, such as for instance due to pressure drop in the plant or the amount of gas in the UHP tank is low or empty, then this pressure switch would divert the gas flow to vent, rather than the analyzer.

As long as the gas maintained at about 50 psi, then the pressure switch is satisfied and allows calibration gas to pass on to the analyzer being calibrated. If the inlet flow gas pressure falls below 40 psi. the pressure switch becomes unsatisfied and causes the excess flow to exit or pass out of the vent. This ensures that same flow is maintained across the permeation devices.

Further, it is desirable to maintain the constant flow across the tubes, but one need not use the full one liter calibration gas in the analyzers, so the unused excess calibration gas is vented through the backpressure regulator.

The apparatus may also have an indicator that alerts an operator if the pressure of the gas in the conduit reaches an undesired pressure. For example, the indicator may comprise various alarms such as visual alarms like lights or auditory type alarms. In an embodiment, also there is a red light indicator 177 warning lights up and alerts the operator in order to prevent calibration with a false calibration gas. See FIG. 4. During normal operation, the indicator light will be green 175.

Further, the apparatus may have insulation 51 within the housing to minimize external temperature influences. Additionally, the type of material used for the housing is also important. Steel for example does not disperse the heat or the cold around the permeation devices and conduit that runs inside the housing. Thus, in an embodiment, the housing 50 and/or case 56 of the apparatus are comprised of aluminum. It is preferable to use completely aluminum boxes because they disperse the heat or coolant very evenly. Also, to prevent temperature fluxuations, the housing is also preferably insulated.

The apparatus may also have a fan 120b within the housing that circulates the air within the housing to ensure an even temperature within the housing. The fan may be positioned near the heater that generates a false ambient temperature. In an embodiment, the generated temperatures are at least about 80° F. to about 85° F., depending on the quality of the heater, but usually it will get us over 80° F., which is usually above room temperature. For further temperature control fan 120a may be positioned outside the housing, such as near the back of the apparatus. Then, the temperature is decreased to maintain a very close tolerance of set point temperature.

The fan keeps the air circulating within the housing, and it can be set up to blow directly onto the surface of the semi-conductor heating device 82, to keep the heated air circulated. There is a resistant temperature device (RTD) 79 that fits in the center of the housing that reads the temperature of the circulated air and goes to temperature controller 190 that controls the temperature in the housing. See. FIG. 4.

Sample gas may be transmitted through the same apparatus used to prepare the calibration gas or may be directed to the instrument in other manners known to one skilled in the art.

If desired, the sample can be analyzed, at the same temperature and flow as the calibration standard. For example, the apparatus may also have a third conduit 40, wherein at least a portion of the third conduit is located within the housing and wherein sample gas can be introduced into the third conduit. See FIGS. 2-3. By running at least a portion of the third conduit through the housing, the gas within the third conduit is similarly heated, cooled, or maintained at ambient temperature. This enables the sample gas to be tested at the same temperature, or approximately same temperature of the calibration gas. This provides a more accurate, precise, and reliable analysis of sample gas.

The sample gas 68 that is introduced into the third conduit 48, such as through connector 59, may vary based upon the type of gas being produced or tested, and may comprise any type of gas that is available for testing. For example, the gas may be production gas, industrial produced gases, gases used in research and development, forensic applications, biomedical gases, and the like. Examples of common types of sample gases include, but are not limited to gases selected from the group consisting essentially of carbon dioxide, nitrogen, oxygen, helium, argon, carbon monoxide, hydrogen, or a combination thereof.

A third solenoid valve 139 controls the flow of the sample gas. See FIGS. 2-3. If analysis of the sample gas is desired, the valve opens and the temperature equilibrated sample gas flows though conduit 40b to the instrument doing the analysis. If the instrument is a gas chromatograph 150, a rotometer 155 is used to ensure steady gas flow.

Various types of tubings may be used for the conduits of this apparatus. Stainless steel is one preferable type of tubing since it can be bent and shaped unlike glass tubings that break. Stainless steel is also more durable than rubber and plastic type tubings. The choice of tubings can be especially important since the calibration gas may be used to calibrate several types of analyzers, and different types of tubing that could be used for gases are affected by chemical components found in purge and sample gases. For example, stainless steel tubing is typically suitable for gas chromatographs, which can be used to analyze gases containing compounds such as benzene, acetaldehyde, or dimethylether. However, sulfur tends to permeate into stainless steel, so by passing sulfur containing standards through stainless steel, some of the sulfur standard would be lost. Further, artificially high readings can occur due to the release of components that previously permeated into the tubing. Thus, sulfur inert tubing, which is actually stainless steel tubing with a liner that is inert to sulfur may be used for the conduit for all or part of the apparatus. Sulfur inert tubing is commercially available and is, for example, manufactured by Restech. The sulfur inert tubing may further be inert to other impurities that are tested for or analyzed.

Thus in this apparatus, at least a portion or the entire main 40 gas conduit may be comprised of tubing that is sulfur inert. Furthermore, if desired, the first 44 and third 48 gas conduits may also be comprised of sulfur inert tubing.

Additionally, in an embodiment, all of the fittings e.g. 160, 170, 61, 71, 59 that come in contact with the gas standards or tubing can also be coated with sulfur inert coating to prevent permeation of the standard into the tubing. It is also thought that the sulfur inert tubing may also have properties to prevent other components from also permeating into the stainless steel.

The apparatus may also comprise a pressure indicator 179 and a pressure regulator, such as a back pressure regulator 180 to ensure that the instruments receive only gas or calibration that has the adequate pressures, if required by the instrument(s)

Furthermore, the apparatus may also have an indicator that alerts an operator if the pressure of the gas in the conduit reaches an undesired pressure.

Additionally, the apparatus may have means 160 to vent gas from the housing to the main conduit if the pressure of the calibration gas drops below about 40- about 45 psi. The apparatus may be programmed or controlled to also vent the gas if it rises above about 100 psi, but that is not typically a problem as there is a pressure regulator on the pure gas to control the gas pressure. With regards to the purge gas, in an embodiment the purge gas may be a stream of gas comes directly from industrial gas production and the pressure of that gas typically is below about 100 psi. Further, the sample gas may also be gas that comes from industrial gas production, and is tested at various time intervals as desired.

Also, this invention may also comprise a backpressure regulator 180 that regulates the pressure of the gas flowing to the analytical instrument(s). Again, it is preferable to keep a steady, set amount of gas flowing with is dependant upon the type and characteristics of the instrument, such as a sulfur analyzer or gas chromatograph. Thus, a back pressure regulator can be used to prevent excess flow to the instrument. Certain instruments also have built-in flow meters.

The apparatus may also further comprise means to convey the calibration gas to at least one instrument. The means may comprise a conduit, a flow controller, a regulator, and any other means known to one skilled in the art for holding gas, controlling gas, or conveying gas.

Additionally, in an embodiment, the apparatus is contained within a portable case.

The apparatus also has means for adjusting the temperature, and flow. The means for adjusting may comprise knobs, button, or other devices used by one skilled in the art to adjust such controls.

The apparatus further preferably has displays for temperature, mass flow, and back pressure. The displays are preferably placed where they are visible, and may be especially useful on the top or the front of the apparatus.

In this apparatus, a 12 volt direct current power supply is preferably used to operate the apparatus.

FIG. 4 shows the circuitry of an embodiment of an apparatus of the invention. For example, a direct current power supply such as a 12 volt power supply 10 is connected to the various components and parts of the invention. A fuse 12 is present for a safety feature. The temperature controller 190 is attached to the power supply and switches 84 that determine whether the apparatus produces heat or cooling within the housing 50. The switch will be directed to the cooling 88 circuit or the heating 86 circuit depending upon the temperature controller. The semi-conductor heating and cooling device 80 is also attached to the power supply and of course is controlled by the temperature controller. A fan 120 in the housing circulates the air within the housing. Further, there is a zero flow switch 99 and a flow shut off 92 that are part of the mass flow controller 90. Further the mass flow controller has a set point 95 and the mass flow controller further has a display outlet and a mass flow display 98. Additionally, the apparatus can be operated manually and has circuit for manual operation 24, and a switch for automatic operation 22. Additionally, the low or purge gas pressure gas switch 100 is also included.

Additionally, a method of producing a gas calibration sample is contemplated by this invention that comprises: providing a source for generating a chosen impurity at a rate having a known value range of nanograms per minute within a given temperature range and a predetermined flow rate; supplying at least one gas conduit; providing an insulated housing; placing the impurity source and at least a portion of the at least one gas conduit within the housing; controlling the temperature within the housing at between about 60° F. and about 130° F. during standby or when calibration is desired; providing a communication between the conduit and the impurity source; providing a supply of pure gas; making a calibration gas by and allowing the impurity source to diffuse into the pure gas that flows past the communication, thereby mixing with the pure gas; and using the calibration gas to calibrate an instrument.

As a further embodiment of this method, a supply of purge gas is supplied, the purge gas is introduced into the at least one conduit, wherein purge gas flows through the conduit during standby and causes the impurity source to diffuse into the purge gas that flows past the communication. Further, when a calibration gas is desired, the purge gas is changed to pure gas.

Again, a calibration gas is made by allowing the impurity source to diffuse into the pure gas that flows past the communication, thereby mixing with the pure gas. The calibration gas can be used to calibrate an instrument.

Also as part of this method, a device is used to selectively raise, lower, or maintain the temperature within the housing between about 60° F. and 130° F. to create the optimal temperature for the chosen impurity source. While the semi-conductor device is preferable, other devices that are capable of raising or lowering the temperature of an interior of the housing may also be used. Those devices include, but are not limited to, a heat exchanger, a conventional coiled heating apparatus, cooling refrigerant, a circuit holding heated and/or cooled fluid that circulates around or within the housing, and the like that are used or known by one skilled in the art.

The method further comprises the steps of analyzing the calibration gas in an instrument, and calibrating an instrument based upon the analysis and the known value of the impurity source.

The method may also further comprise providing a sample gas for analysis, and then the step of analyzing the sample gas in the calibrated instrument.

Also in this method, at least a portion of conduit may comprise tubing that has a sulfur inert interior.

Further in this method, the instrument may comprise a sulfur analyzer, a gas chromatograph, gas monitoring system, or a hydrocarbon analyzer. Other such instruments that are used to test gases that are known or used to one skilled in the art, may also be calibrated with a calibration gas or liquid produced by this apparatus.

In an embodiment of this method, the impurity is generated at about 10 nanograms per minute to about 50 nanograms per minute.

The impurity source produces at least one impurity of a known concentration of about 10 nanograms per minute to about 50 nanograms per minute, or more, that is measurable in ppm, ppb, or ppt.

Further, if only a main conduit is used to hold and convey gas, the purge gas and the pure gas are introduced into the same conduit at different times.

However, in an alternative embodiment, at least one additional conduit is supplied for sample gas.

In this method, the purge gas is comprised essentially of carbon dioxide, nitrogen, oxygen, helium, argon, carbon monoxide, hydrogen, or a combination thereof, or any other gases that are useful as a purge gas that are known or used by one skilled in the art. Preferably, the purge gas will be less expensive to use than pure gas and will typically be less pure than pure gas.

Also, the impurity source supplies at least one impurity of a concentration measurable in ppm and/or ppb.

Further as part of this method, a flow controller may be used to control the flow of gas inside the conduit between zero liters per minute to about two liters per minute. Applicants use an electronic flow controller, like a mass flow controller, which allows the operator to choose a set point voltage and then the flow controller will maintain the proper flow across the tubes.

Also, a backpressure regulator may be connected to the conduit prior to the instrument.

Downstream from the valve, a pressure switch may be included. In an embodiment, the pressure is kept at approximately 40 psi to maintain the correct pressure to operate the intact total sulfur analyzers that require about 30 psi to about 35 psi of pressure on the inlet. The calibration gas comes out as a combined gas, which then brings them to out to a small header, which has a back pressure regulator on it, which is what is used to actually hold the approximately 40 psi of back pressure, so that there is constant pressure, constant flow and then all of this is controlled, with a temperature controllers, so that constant temperature is maintained.

Also, a rotometer 155 may be used to ensure a steady gas flow to the instrument. See FIG. 1.

A system for providing a more accurate calibration of instruments for testing gases is also contemplated by this invention. The system comprises: at least one source that generates at least one chosen impurity in a known range of nanograms per minute at a known temperature range and at a predetermined flow rate, a supply of pure gas, a main gas conduit, a housing having an interior that holds the source of the at least one purity and at least a portion of the main conduit, a means for selectively raising and/or lowering the temperature of the housing interior between about 60° F. and 130° F., wherein the temperature of the source and the at least a portion of the main conduit is selectively raised and/or lowered between about 60° F. and about 130° F., a flow controller that allows gas to flow through the main conduit between about 0.5 liters/minute and about 2 liters/minute, a communication between the impurity source and the main conduit, wherein pure gas flows through the main conduit and past the communication wherein the impurity source diffuses into the pure gas and mixes with the pure gas to form a calibration gas, an instrument that is capable of being calibrated, a connection between the instrument and the main conduit, wherein the calibration gas is fed to the instrument that analyzes the gas, wherein the instrument is calibrated based the analysis and the known value of the source.

In a further embodiment, the system comprises: a supply of purge gas, a valve, wherein the valve determines whether the pure and/or purge flows into the main gas conduit, wherein purge gas is run through main conduit during standby and pure gas is run through the main conduit when calibration is desired.

In another alternative embodiment, the system comprises: a first gas conduit, a second gas conduit, and a valve connecting the first and second conduits to the main conduit, wherein the valve determines which gas will flow into the main conduit; a supply of purge gas, wherein purge gas flows through the second gas conduit, and wherein pure gas flows through the first gas conduit; wherein the pure gas is introduced into first the conduit when calibration is desired and wherein purge gas can be introduced into the second conduit when calibration gas is not needed, wherein either pure gas or purge gas is introduced into the main conduit and flows past the communication; and wherein the valve is changed to stop the flow of purge gas into the main conduit and pure gas is allowed to flow through the first conduit into the main conduit when calibration is desired.

In an embodiment of this system, the main conduit is comprised of sulfur inert tubing.

Further, this system may also include a chart showing the known concentration ranges of a certain impurity from the source in ppm or ppb at a certain temperature range.

In the preferred embodiment of this system, the means for selectively raising and/or lowering the temperature is comprised of a semi-conductor heating and cooling device.

Also in this system, it is preferable to use purge gas in the main conduit during standby to allow the impurity from the source to continually diffuse into the flowing purge gas so that there is not a build up of the impurity which would cause an inaccurate calibration.

Additionally, in this system, the purge gas may be comprised essentially of carbon dioxide, nitrogen, oxygen, helium, argon, carbon monoxide, hydrogen, or a combination thereof.

In this system, at least one instrument can be calibrated based upon the analysis and the known value of the calibration gas. Further in this system, a gas sample comprising an unknown amount of impurity for analysis, can be analyzed by the calibrated instrument. Also, the sample analysis yields a result, and the result of the sample analysis is compared with known results to determine the type and amount of impurities in the sample.

In this system, the instrument may comprise a gas chromatograph, a sulfur analyzer, a hydrocarbon analyzer, a gas monitoring system, or other such analytical instruments known or used by one skilled in the art for analyzing and/or quantifying gases.

This system may comprise a rotometer between the main conduit and the gas chromatograph.

While preferred embodiments of the present invention have been disclosed, it will be readily apparent to those of ordinary skill in the art that many modifications may be made and for a further understanding of the nature and scope of the present invention, attention should be had to the appended claims. Further, although specific forms of the invention have been selected for illustration and discussed in the preceding description is drawn in specific terms for the purpose of describing these forms of the invention fully and amply for one of average skill in the pertinent art, it should be understood that various substitutions and modifications which bring about substantially equivalent or superior results and/or performance are deemed to be within the scope and spirit of the following claims.

We claim:

1. An apparatus for providing gases for calibration, comprising:
   at least one source that generates at least one chosen impurity in a known range of nanograms per minute within given temperature ranges and at a predetermined flow rate;
   a supply of gas that is at least substantially pure;
   a supply of purge gas;
   a main gas conduit;
   a communication between said at least one impurity source and at least a portion of said main conduit;
   a housing having an interior, wherein said impurity source and at least a portion of said main conduit is located within the interior of said housing;
   a means for selectively raising and/or lowering the temperature of the housing interior between about 60° F. and about 130° F., wherein the means for selectively raising and/or lowering the temperature comprises a temperature controller that controls the temperature within said housing and a semi-conductor heating and cooling device; and
   a valve that connects the supply of pure gas and the supply of purge gas to the main conduit,
   wherein:
      said pure gas flows through said main conduit and passes by said communication,
      the impurity from said source diffuses into said pure gas that flows past said communication thereby producing a calibration gas; and
      the purge gas and the pure gas are introduced into the main conduit at different times.

2. The apparatus of claim 1, further comprising a first gas conduit a second gas conduit, and a valve connecting the first and second conduits to said main conduit, wherein said pure gas is introduced into first said conduit when calibration is desired and wherein purge gas can be introduced into said second conduit when calibration gas is not needed, and wherein said valve determines which gas will flow into said main conduit.

3. An apparatus for providing gases for calibration, comprising:
   at least one source that generates at least one chosen impurity in a known range of nanograms per minute within given temperature ranges and at a predetermined flow rate;
   a supply of gas that is at least substantially pure;
   a main gas conduit;
   a communication between said at least one impurity source and at least a portion of said main conduit;
   a housing having an interior, wherein said impurity source and at least a portion of said main conduit is located within the interior of said housing;
   a means for selectively raising and/or lowering the temperature of the housing interior between about 60° F. and about 130° F.;
   a temperature controller that controls the temperature within said housing;
   a pressure indicator and a back pressure regulator that monitors the pressure of gas in said main conduit and regulates the flow path of said gas;
   a means to vent gas from said main conduit if the pressure of the calibration gas drops below about 35 psi to about 40 psi; and wherein said pure gas flows through said main conduit and passes by said communication, and wherein the impurity from said source diffuses into said pure gas that flows past said communication thereby producing a calibration gas.

4. A method of producing gases for calibration, comprising:
providing a source for generating a chosen impurity at a rate having a known value range of nanograms per minute within given temperature ranges and a predetermined flow rate;
supplying at least one gas conduit;
providing an insulated housing;
placing the impurity source and at least a portion of said at least one gas conduit within said housing;
controlling the temperature within said housing at between about 60° F. and about 130° F. during standby or when calibration is desired;
providing a communication between the said conduit and said impurity source;
providing a supply of pure gas;
making a calibration gas by and allowing the impurity source to diffuse into said pure gas that flows past said communication, thereby mixing with said pure gas;
using the calibration gas to calibrate an instrument;
providing a supply of purge gas;
introducing purge gas into said at least one conduit, wherein purge gas flows through said conduit during standby and causes the impurity source to diffuse into said purge gas that flows past said communication; and
changing the purge gas to pure gas when a calibration gas is desired.

5. The method of claim 4, wherein the purge gas and the pure gas are introduced into the same conduit at different times.

6. A method of producing gases for calibration, comprising:
providing a source for generating a chosen impurity at a rate having a known value range of nanograms per minute within given temperature ranges and a predetermined flow rate;
supplying at least one gas conduit;
providing an insulated housing;
placing the impurity source and at least a portion of said at least one gas conduit within said housing;
controlling the temperature within said housing at between about 60° F. and about 130° F. during standby or when calibration is desired;
providing a communication between the said conduit and said impurity source;
providing a supply of pure gas;
making a calibration gas by and allowing the impurity source to diffuse into said pure gas that flows past said communication, thereby mixing with said pure gas;
using the calibration gas to calibrate an instrument;
providing a first conduit, a second conduit, and a valve connecting said first and second conduits to said at least one conduit, wherein said at least one conduit is the main gas conduit;
providing a supply of purge gas;
connecting said supply of pure gas to said first conduit;
connecting said supply of purge gas to said second conduit;
running purge gas through said second conduit during standby and opening said valve so that purge gas is introduced into the main conduit and flows past said communication; and
changing said valve to stop the flow of purge gas into said main conduit and allowing pure gas to flow through said first conduit into said main conduit when calibration is desired.

7. A system for providing a more accurate calibration of instruments for testing gases, comprising:
at least one source that generates at least one chosen impurity in a known range of nanograms per minute at a known temperature range and at a predetermined flow rate;
a supply of pure gas;
a main gas conduit;
a housing having an interior that holds the source of said at least one purity and at least a portion of said main conduit;
a means for selectively raising and/or lowering the temperature of the housing interior between about 60° F. and 130° F., wherein the temperature of said source and said at least a portion of said main conduit is selectively raised and/or lowered between about 60° F. and about 130° F.;
a flow controller that allows gas to flow through said main conduit between about 0.5 liters/minute and about 2 liters/minute;
a communication between said impurity source and said main conduit, wherein pure gas flows through the main conduit and past said communication wherein said impurity source diffuses into the pure gas and mixes with said pure gas to form a calibration gas;
an instrument that is capable of being calibrated;
a connection between said instrument and said main conduit, wherein said
calibration gas is fed to the instrument that analyzes said gas; wherein said instrument is calibrated based said analysis and the known value of said source
a supply of purge gas;
a valve, wherein said valve determines whether said pure and/or purge flows into said main gas conduit; and
wherein purge gas is run through main conduit during standby and pure gas is run through said main conduit when calibration is desired.

8. A system for providing a more accurate calibration of instruments for testing gases, comprising:
at least one source that generates at least one chosen impurity in a known range of nanograms per minute at a known temperature range and at a predetermined flow rate;
a supply of pure gas;
a main gas conduit;
a housing having an interior that holds the source of said at least one purity and at least a portion of said main conduit;
a means for selectively raising and/or lowering the temperature of the housing interior between about 60° F. and 130° F., wherein the temperature of said source and said at least a portion of said main conduit is selectively raised and/or lowered between about 60° F. and about 130° F.;
a flow controller that allows gas to flow through said main conduit between about 0.5 liters/minute and about 2 liters/minute;
a communication between said impurity source and said main conduit, wherein pure gas flows through the main conduit and past said communication wherein said impurity source diffuses into the pure gas and mixes with said pure gas to form a calibration gas;
an instrument that is capable of being calibrated;

a connection between said instrument and said main conduit, wherein said
calibration gas is fed to the instrument that analyzes said gas;
wherein said instrument is calibrated based on said analysis and the known value of said source;
a first gas conduit, a second gas conduit, and a valve connecting the first and second conduits to said main conduit, wherein said valve determines which gas will flow into said main conduit;
a supply of purge gas, wherein purge gas flows through said second gas conduit, and wherein pure gas flows through said first gas conduit;

wherein said pure gas is introduced into first said conduit when calibration is desired and wherein purge gas can be introduced into said second conduit when calibration gas is not needed, wherein either pure gas or purge gas can be introduced into the main conduit to flow past said communication; and wherein said valve is changed to stop the flow of purge gas into said main conduit and pure gas is allowed to flow through said first conduit into said main conduit when calibration is desired.

* * * * *